(12) United States Patent
Ronco et al.

(10) Patent No.: US 9,506,022 B2
(45) Date of Patent: Nov. 29, 2016

(54) CELLULOSE-BASED DISAGGREGATABLE PAPER CONTAINING DETERGENTS

(71) Applicant: Danilo Ronco, Villanova Solaro (IT)

(72) Inventors: Danilo Ronco, Villanova Solaro (IT); Claudio Bozzi, Milan (IT); Gianfranco Crippa, Voghera (IT); Davide Mariani, Cilavegna (IT)

(73) Assignee: Danilo Ronco, Villanova Solaro (IT)

( * ) Notice: Subject to any disclaimer, the term of this patent is extended or adjusted under 35 U.S.C. 154(b) by 0 days.

(21) Appl. No.: 14/377,812

(22) PCT Filed: Feb. 21, 2013

(86) PCT No.: PCT/IB2013/051401
§ 371 (c)(1),
(2) Date: Aug. 8, 2014

(87) PCT Pub. No.: WO2013/124804
PCT Pub. Date: Aug. 29, 2013

(65) Prior Publication Data
US 2015/0152369 A1    Jun. 4, 2015

(30) Foreign Application Priority Data
Feb. 24, 2012    (WO) .................... CN2012A000004

(51) Int. Cl.
| | | |
|---|---|---|
| A01N 25/34 | (2006.01) |
| A61K 47/32 | (2006.01) |
| C11D 3/20 | (2006.01) |
| D21F 11/00 | (2006.01) |
| D21H 23/00 | (2006.01) |
| D21H 21/00 | (2006.01) |
| D21H 17/00 | (2006.01) |
| C11D 17/04 | (2006.01) |
| A61K 8/73 | (2006.01) |
| A61Q 19/10 | (2006.01) |
| A61K 8/02 | (2006.01) |
| C11D 3/00 | (2006.01) |
| C11D 3/22 | (2006.01) |
| C11D 3/38 | (2006.01) |
| C11D 1/94 | (2006.01) |
| D21H 21/14 | (2006.01) |

(52) U.S. Cl.
CPC .......... *C11D 17/044* (2013.01); *A61K 8/0208* (2013.01); *A61K 8/0216* (2013.01); *A61K 8/731* (2013.01); *A61Q 19/10* (2013.01); *C11D 1/94* (2013.01); *C11D 3/0021* (2013.01); *C11D 3/222* (2013.01); *C11D 3/225* (2013.01); *C11D 3/38* (2013.01); *C11D 17/049* (2013.01); *D21H 21/14* (2013.01); *A61K 2800/805* (2013.01)

(58) Field of Classification Search
None
See application file for complete search history.

(56) References Cited

U.S. PATENT DOCUMENTS

| | | |
|---|---|---|
| 2,648,635 A | 8/1953 | Russell et al. |
| 4,532,063 A | 7/1985 | Gueldenzopf |
| 5,062,986 A | 11/1991 | Fujita |
| 6,190,502 B1 | 2/2001 | Takeuchi |
| 2008/0242572 A1 | 10/2008 | Icht |
| 2009/0202582 A1 | 8/2009 | Irrgang |

FOREIGN PATENT DOCUMENTS

| | | | |
|---|---|---|---|
| DE | 19640086 | 4/1998 | |
| EP | 0 357 496 A2 * | 3/1990 | ............. A47L 13/17 |
| EP | 0 992 338 A2 * | 4/2000 | ............... B32B 5/26 |
| FR | 2120295 | 8/1972 | |
| GB | 488291 | 7/1938 | |
| JP | 2001-98489 | 10/2002 | |
| JP | 2003-119498 | 4/2003 | |
| WO | 2004087857 | 10/2004 | |

OTHER PUBLICATIONS

Nature Clean Natural Liquid Soaps (web.archive.org/web/20120213171545/http://www.naturecleaningliving.com/natural_liquid_soaps); 2 pages; dated Feb. 13, 2012; downloaded Nov. 6, 2015.*
Piret et al.; Current Drug Targets, 2002, 3, 17-30.*

* cited by examiner

*Primary Examiner* — Jeffrey T Palenik
(74) *Attorney, Agent, or Firm* — Stradley Ronon Stevens & Young, LLP

(57) ABSTRACT

A soaped paper which will disaggregate in aqueous liquids comprising:
  a. cellulose-based fiber pulp: 50-90% by weight;
  b. disaggregating agent: 30-3% by weight;
  c. at least one detergent;
  is described.
The preferred disaggregating agent is the sodium salt of carboxymethylcellulose. This paper can be used to wash parts of the body of people or animals; it is also dry, may be available in the form of rolls, does not leave residues which have to be disposed of and is produced using automatic industrial processes.

20 Claims, 2 Drawing Sheets

CELLULOSE-BASED DISAGGREGATABLE PAPER CONTAINING DETERGENTS

Figure 1:
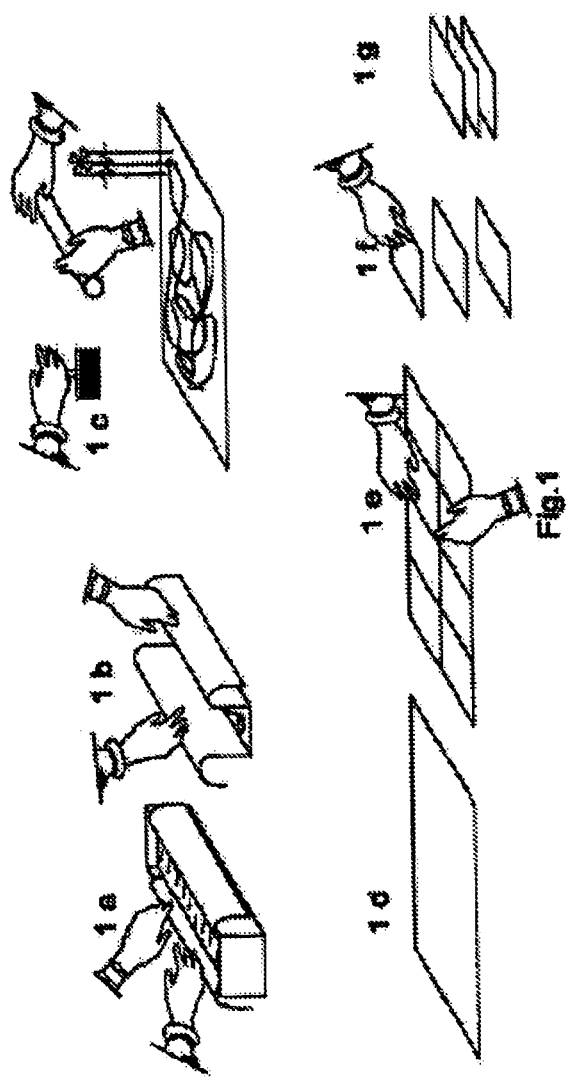

This invention relates to the field of paper chemistry, in particular a soluble soaped paper which can be used to wash parts of persons' or animals' bodies; specifically it relates to a dry paper available in the form of a roll which is impregnated with surfactants, does not leave any wastes that have to be disposed of and is manufactured through automatic industrial processes.

BACKGROUND TO THE INVENTION

The production and use of sheets of cellulose-based paper that are impregnated with surfactants and are wholly water-soluble are known. However the terminology used for the substrate or the final product, paper or tissue, is not always uniform and is sometimes a source of confusion and misunderstandings.

In the paper industry, by paper is meant a felt of vegetable fibres whose main components are cellulose and lignin, obtained from a suspension of such fibres in water. Conversion from a suspension to felt is achieved through draining on a clothing. The thin sheet so obtained has magnitudes in two dimensions, width and length, which are many orders greater than the third, its thickness.

In the meaning of this invention, by paper is meant a product containing at least 50% of cellulose or cellulose and lignin. In the meaning of this invention known products having a lower percentage are not regarded as being paper. GB656210 describes a tissue which can be used as a substitute for soap formed of water-soluble cellulose ether fibres and surfactants (e.g. alkyl sulphates) which may contain the sodium salt of carboxymethylcellulose as the binding agent between the fibres. The process of producing the substrate known as "tissue" may be obtained using paper production technology, but the starting material comprises cellulose ethers. The tissue is therefore obtained by forming a pulp of cellulose ether fibres in a liquid which also contains surfactants; this pulp is then spread onto a forming grid to form a "feltrate" layer from which the liquid is drained and the remaining liquid is removed by evaporation. The starting material used to obtain the tissue to which the patent relates is always a water-soluble fibrous material, preferably a cellulose ether or alternately an alginate or polyvinyl alcohol. In the patent cellulose is only cited as the starting material (reagent) in order to obtain the methyl cellulose. Thus the material used to form the substrate (cellulose ethers) differs from cellulose. The product described cannot be regarded as paper, in that the starting material does not provide at least 50% of cellulose or cellulose and lignin.

EP0003186 describes wet wipes of high mechanical strength obtained by adding a binding agent, polyvinyl alcohol (PVA, PVOH), to a substrate described as "non-woven fabric" (which by definition is different from paper because in non-woven fabric dimensional stability is imparted by a polymer matrix and not by the inter-fibre hydrogen bonds of cellulose). The substrate containing PVA must subsequently be treated with products (boric acid and water-soluble salts) to ensure that the material so obtained (wipes) is dimensionally stable when placed in contact with water. The wipes have good resistance to moisture but break up (disaggregate) when immersed in water and subjected to agitation. In the examples it is learnt how the required mechanical strength is only obtained after the paper has been processed with polyvinyl alcohol and boric acid. In addition to this, disaggregation is accomplished only by providing a certain amount of external energy, in particular mechanical energy.

EP0896089 describes substantially the same product as EP0003186, but with greater accuracy and precision, and with some changes in the formulation of the products added to the substrate. In this case explicit reference is made to paper (fibrous sheet such as paper) to which is added a binding agent (binder), polyvinyl alcohol (PVA), through surface treatment. Subsequently a carboxylate is added to the paper containing PVA to impart sufficient strength to the sheet for it to be rubbed even when it is soaked. In the description a disintegration time for the wipe is quantified through a test which provides for the use of a rotor at increasing rotation speed. Disintegration of the wipe in water therefore requires the application of a certain amount of energy.

CA233748 describes a disposable soap comprising a substrate dissolving in water which is impregnated with a cleansing composition placed in a container. This substrate may be a tissue, and paper is understood to be the material. This reference only describes individual sheets (wipes). The possibility of producing a roll is never mentioned.

WO2005060931 describes cleansing wipes formed of a single layer which dissolve in contact with water, comprising a polymer material forming a water-soluble film (70-98%) containing materials which are soluble and/or dispersible in water, and a cleansing agent (1-30%). They may also possibly contain an abrasive cleansing agent or a fibrous filler which may comprise wood fibre, therefore also cellulose, in quantities from 1 to 20%. Cellulose is not mentioned among the materials which can be dispersed in water. An essential feature of the product described is its suitable wet strength which enables it to maintain an intact structure for a sufficient time for cleansing.

In the documents of the state of the art described above there are therefore descriptions of wipes or tissues with good wet strength that are capable of sustaining a rubbing action against the skin. These disintegrate when they are subjected to a high flow of water but in the additional presence of significant mechanical action providing energy.

Furthermore the products described in documents GB656210 and WO2005060931 do not fall within the scope of the conventional definition of "paper" because the latter provides for the presence of vegetable fibre, the main components of which are cellulose or cellulose and lignin in a quantity in excess of 50%.

JP2003082397 and JP2003073700 describe a water-soluble soaped paper comprising an alkaline salt of carboxymethylcellulose (CMC) and wood pulp. However as in the case of documents GB656210 and WO2005060931 these products do not fall within the scope of the conventional definition of "paper" because the latter provides for the presence of vegetable fibre, the main components of which are cellulose or cellulose and lignin, in a quantity in excess of 50%.

JP2003082397 also provides for the presence of a component which retains moisture. The paper is obtained by mixing carboxymethylcellulose and wood pulp in proportions of approximately 75-85 and 15-25 respectively, and drying. The soluble paper is then coated with liquid soap and dried by heat.

One of the essential features of the soaped soluble paper described in the abovementioned Japanese patents is that they are wholly soluble in water.

The present inventors are aware of a soaped paper which will disaggregate in water, which is prepared by hand by craft means. The craft production cycle provides for placing a solution of water and cellulose fibres in a vessel (FIG. 1a) which deposits out through gravity onto a forming cloth; this forming cloth is subsequently lifted from the water, draining off a good part of the excess water. A cellulose paste remains on the forming cloth (FIG. 1b) and is subsequently spread out (FIG. 1c), manually impregnated with soap solution, dried by means of hot air jets and finally rolled up. This process carried out on a craft basis makes it possible to produce limited quantities of soaped paper. Because of its intrinsic characteristics and small dimensions the soaped paper sheet obtained cannot be rolled up and is therefore cut into small pieces which are subsequently stacked (FIGS. 1d, 1e, 1f and 1g). The small sizes of the hand-made product (individual sheets) so obtained will not allow it to be produced industrially in rolls of desired length and width. This is an impediment to its storage and automatic production on an industrial scale.

An industrial process for obtaining soluble paper which can be wound into rolls is known and implemented by the Aquasol company (Aquasol Corporation, 80 Thompson Street/North Tonawanda, N.Y. 14120). The company produces Aquasol® Water Soluble Paper, a soluble paper characterised by the property that it can quickly disaggregate in water and is available in a variety of thicknesses and sizes, including rolls and sheets. This soluble paper is not however soaped, neither is it impregnated with any substance.

In the light of the state of the art described above there is still a need for a process that makes it possible to obtain a completely water-soluble soaped paper which can be made available in various formats, in particular in the form of a roll, produced through a continuous industrial process.

SUMMARY OF THE INVENTION

This invention overcomes the technical problems described above through a new process through which a dry soaped soluble paper having consistency and flexibility such that it can be rolled and unrolled while maintaining the physical characteristics of ordinary paper is obtained. This paper can then be stored in rolls of any size without this giving rise to any damage or deterioration during the operations of winding or unwinding the roll.

The process according to this invention also makes it possible to produce soluble soaped paper using an automatic continuous industrial production system with consolidated technology known in the art because it is used in the production of normal paper.

Use of the product according to this invention as a substitute for liquid soap also makes it possible to reduce environmental impact through the possibility of metering the surfactant placed on the paper substrate, offering savings of more than 90% by weight and volume of the liquid soap.

This type of paper is the subject matter of this invention. It is characterised in particular by being soft, flexible, soluble in aqueous liquids and containing cleansing agents. Preferably the soaped paper according to this invention is soluble in water, water-alcohol solutions and other solutions commonly used for cleansing the body.

The weight of the paper obtained is not critical, and may vary from the minimum which can be achieved that is compatible with use of the paper. Preferably the weight varies between 20 and 500 g/m$^2$.

It can also be written and printed upon. It is in fact possible to write on the paper with a pen or pencil or to apply multicoloured inks in order to produce figures or writing.

DESCRIPTION OF THE INVENTION

Definitions

For the purposes of this invention the term "paper" is taken to mean a felt of virgin and/or regenerated vegetable fibres of any origin (for example wood pulp, mechanical pulps, semi-chemical pulps, chemical pulps, cotton linter, annual plants, etc.) whose main components are cellulose or cellulose and lignin having a minimum content of 50% by weight, obtained from a suspension of such fibres in water.

In the context of this invention, by soluble paper is meant a paper which disaggregates, dissociating into single fibres, in contact with an aqueous liquid, for example water, water and alcohol, or water in a mixture with other solvents. In this invention "soluble" paper is also indicated by the term "disaggregatable", meaning full disaggregation with slight manual agitation, without the assistance of laboratory mechanical means. The user perceives this disaggregation as being "soluble".

In the context of this invention, by soaped paper is meant a paper impregnated with detergents.

OBJECTS OF THE INVENTION

One object of this invention is a soaped paper which will disaggregate in aqueous liquids, comprising:
a. cellulose-based fibre pulp: 50-90% by weight;
b. disaggregating agent: 30-3% by weight;
c. at least one detergent.

The percentages by weight are calculated in the absence of water.

Another object of this invention is a continuous process for the production of this paper, in particular production in rolls.

Use of the paper for cleansing the human body, in particular the skin, is also an object of this invention.

Further objects of this invention are use of the paper to provide a vehicle for active ingredients and/or medicinal ingredients in general, to provide a vehicle for disinfecting agents for dispersion in water, to provide a vehicle for products which make it possible to wash garments of different colours in a washing machine.

This and other objects of this invention will be illustrated in detail below including by means of examples and figures.

FIGURES

FIG. 1: Example of a known craft production cycle for the production of soaped soluble paper.

Figure 2:
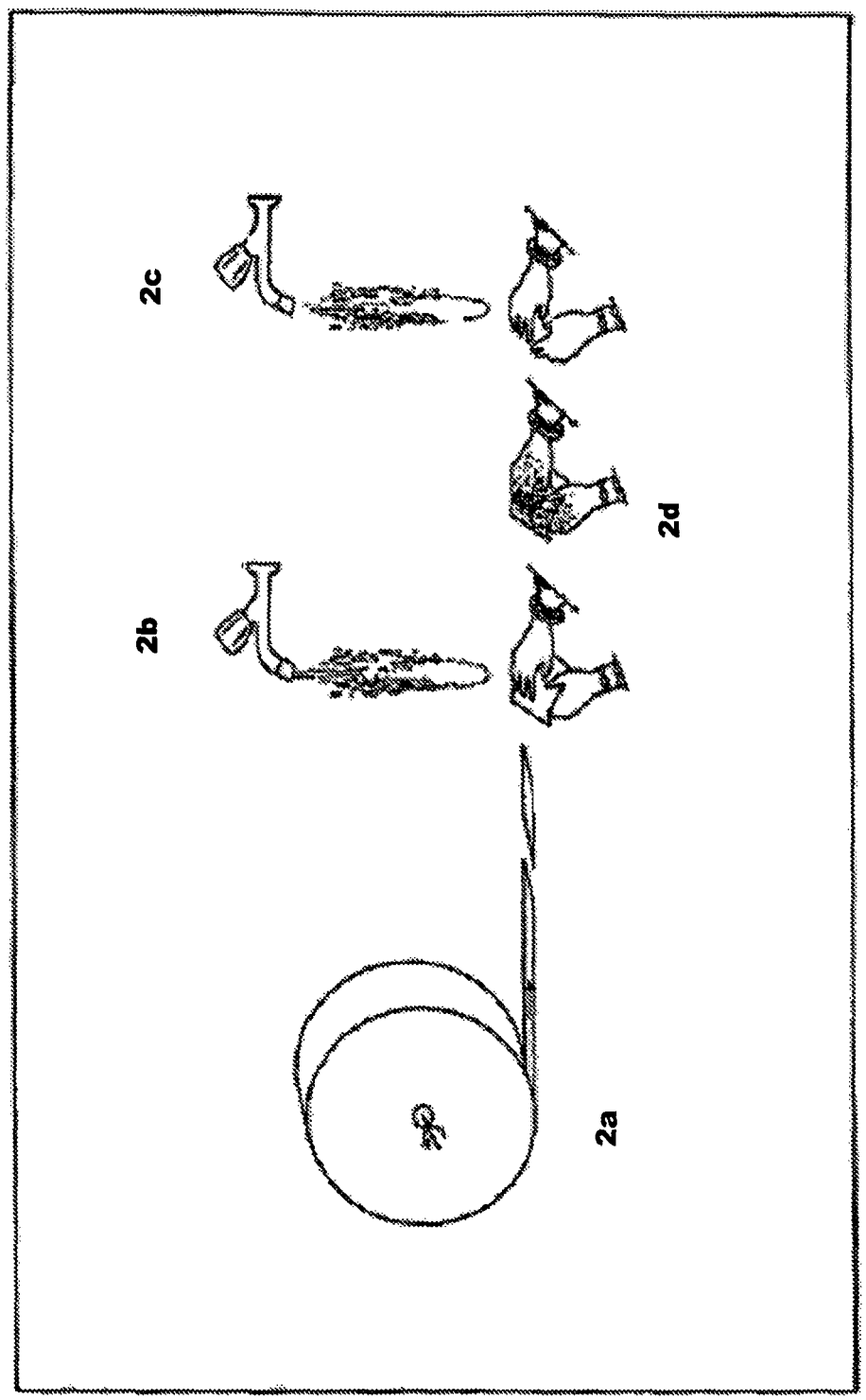

FIG. 2: Illustration of a method of using the paper according to this invention.

DETAILED DESCRIPTION OF THE INVENTION

For the production of disaggregatable (otherwise referred to as soluble) soaped paper that is the subject matter of this invention any material which is suitable for the manufacture of paper is used as a starting material. These materials are well known to those skilled in the art.

In a preferred embodiment of this invention a first cellulose-based fibrous material (cellulose fibre pulp) is used. All the raw materials used for paper may be used as the starting material. In particular mechanical pulps, semi-chemical pulps, chemical pulps, conifer or broadleaf pulps, cotton linters, annual plants and cellulose used for the preparation of the fluff of absorbent auxiliaries, the main components of which are cellulose or cellulose and lignin. Cellulose is a preferred raw material.

To this fibrous material there is added a disaggregating agent in the form of a water-soluble substance (for example molecules, polymers, oligomers, organic and inorganic salts). Examples of water-soluble substances which are suitable for this invention are polymers based on polyvinyl pyrrolidone, polyethylene glycol, xanthan gum, guar gum, polyquaternium polymers, pullulan, hydroxypropylmethyl cellulose, hydroxyethyl cellulose, hydroxylpropyl cellulose, gelatin, the sodium salt of carboxymethylcellulose, polyvinyl alcohol, sodium alginate, gum tragacanth, acacia gum, gum arabic, polyacrylic acid, methyl methacrylate copolymer, carboxyvinyl polymer, amylases, natural and modified starches, aluminium starch octenylsuccinate, hydroxypropyl starch phosphates, high amylase starch, high amylase hydroxypropylate starch, dextrin, pectin, chitin, chitosan, levan, elsinan, collagen, zein, gluten, soya protein isolate, milk protein isolate, casein, carob bean gum, karaya gum, carrageenan, gellan gum, agar, alginic acid and alginates, furcellaran, polyhydroxy acid polymers and mixtures thereof; polysaccharides normally used in paper technology. The preferred disaggregating agent is the sodium salt of carboxymethylcellulose.

A debonding agent (for example ethoxylate/propoxylate alcohols), inorganic and organic dyes, mineral pigments (for example kaolin, calcium carbonate), and retention agents (for example acrylamides, polyamines, cationic silica) may be added. These components may be in liquid or powder form.

In a preferred embodiment of this invention the paper has the following composition, calculated in the absence of water, in which the above-listed components are present in the following percentages:
 cellulose-based fibre pulp: 50-90%, preferably 80-90%,
 disaggregating agent: 3-20%, preferably 5-13%,
 debonding: 2-8%,
 dyes: 0.01-0.05%,
 mineral pigments: 0.1-20%,
 retention agents: 0.1-5%,
 at least one detergent.

The precise percentages of the above-listed components are established from time to time on the basis of paper weight, the solubility of the paper and the physical/mechanical, morphological and printing properties which it is desired to achieve (for example tensile strength, smoothness, thickness, opacity, rigidity, permeability to air, tear resistance, inter-fibre bonding, delamination, whiteness).

In a particularly preferred embodiment the disaggregatable soaped paper according to this invention has the following composition:
 bleached eucalyptus chemical pulp 86.4% by weight;
 sodium salt of carboxymethylcellulose 8.3% by weight;
 debonding agent 5.3% by weight;
 sodium lauryl ether sulphate and lauramidopropyl betaine in a weight ratio of 1 to 1, in the quantity applied to the paper of 8 g/m$^2$;
having a weight of 70 g/m$^2$.

In another particularly preferred embodiment the disaggregatable soaped paper according to this invention has the following composition:
 bleached eucalyptus chemical pulp 57.6% by weight;
 bleached conifer chemical pulp 28.8% by weight;
 sodium salt of carboxymethylcellulose 8.3% by weight;
 debonding agent 5.3% by weight;
 sodium lauryl ether sulphate and lauramidopropyl betaine in a weight ratio 1 to 1, in the applied quantity of 8 g/m$^2$;
having a weight of 70 g/m$^2$.

In another particularly preferred embodiment the disaggregatable soaped paper according to this invention has the following composition:
 bleached eucalyptus chemical pulp 86.4% by weight;
 sodium salt of carboxymethylcellulose 8.3% by weight;
 debonding agent 5.3% by weight;
 sodium lauryl ether sulphate, lauramidopropyl betaine and benzalkonium chloride, in the respective percentages by weight of 49.6, 49.6 and 0.8%. The quantity of surfactant applied to the paper is 8 g/m$^2$;
with a weight of 70 g/m$^2$.

The equipment which can be used for production of this invention is wholly comparable to the technology already present in the production, improvement and reprocessing of paper.

Such equipment comprises:
 a plant for the preparation of pulp, which feeds the feed box of a continuous machine with forming clothing, or alternatively a forming roller (round shaping);
 a press unit;
 a drier, in which a surface treatment unit may be inserted, for example a size press;
 an optional machine smoother;
 a Pope roller;
 an impregnating unit;
 a post-drying unit.

In particular the fundamental components of the paper production line are illustrated below.

A plant for the preparation of pulp, in order to prepare the correct mixture of water, fibres and additives, which is constant over time so that the feed box and the continuous machine can have a uniform feed.

Once the pulp has been prepared, this is fed to the feed box. The feed box is fed with a pulp consistency of the order of 0.4-1% and forms a uniform layer of water, fibres and additives of the same width as the entire continuous machine. The pulp then passes onto the clothing. The stage of dewatering of the pulp begins on the clothing of the continuous machine and the stage of felting the fibres takes place at the same time, in a first stage through natural drainage and then through drainage under vacuum. This type of machine may be replaced with clothing wound into a round shape.

The stage of dewatering the pulp continues with different technologies along the entire length of the continuous machine. Initially the diluted pulp is drained on the clothing, and then passes to the press unit.

The subsequent press unit is designed to continue the process of dewatering the sheet through mechanical pressing systems. This system is very convenient from the energy point of view but it is difficult to achieve dryness values of more than 50-52% dryness.

There follows the drier, where the sheet is dried to the desired degree of dewatering. This consists of causing the wet sheet to adhere to hollow rollers (generally of diameter 1500 mm) within which saturated steam is caused to condense. This system may be incorporated with or sometimes replaced by other drying systems such as hot air stoves, and infrared ray systems.

A surface treatment unit, for example a size press or a film press, may be incorporated in the drier in order to obtain surface treatment of the sheet.

A machine smoother whose purpose is to smooth the paper and generally improve its graphic quality may also be further provided.

Subsequently the continuous sheet passes to a Pope 'reel which continuously' winds the paper produced into a roll and changes rolls without interrupting the production cycle.

A machine such as described above is capable of continuous industrial production of the paper substrate required for this invention.

The roll is then passed to the stage of impregnating the substrate with detergent agents (detergents). The impregnating unit may be off-line, or incorporated in the continuous machine.

In a preferred embodiment the paper is produced in the format of a roll. In this embodiment the equipment provides for the presence of a rolling section, comprising a support around which the paper can be wound, after the drier.

In general the process of preparing paper according to this invention comprises the following stages:
 a. preparing a cellulose-based fibre pulp;
 b. producing a paper substrate by means of a continuous machine;
 c. optional surface treatments on the sheet;
 d. optional smoothing;
 e. impregnation with detergents;
 f. winding and optional packaging.

In greater detail the process according to this invention comprises:
 preparation of a cellulose-based fibre pulp;
 felting the said pulp and dewatering the sheet to an indicative value of approximately 95%;
 optional surface treatment of the sheet;
 optional smoothing;
 winding;
 impregnation with detergents;
 drying to approximately 95%;
 final winding and, if desired, packaging.

A process for preparation of the paper according to this invention will now be described.

The stages and preparation of the paper up to the addition of detergents are wholly conventional and fall within the normal knowledge of those skilled in the art.

The starting fibrous material (cellulose fibre pulp) is placed in and broken up in the vessel of a pulper containing water in order to separate the fibrous material into individual fibres. The disaggregating agent according to this invention and the usual components are then added. Use of this pulper is included in the known art in the context of paper production.

An aqueous suspension containing fibres and the other components described above in a quantity which can vary from 0.7 to 4% by weight of the whole is thus obtained.

The above suspension reaches a flow box which distributes it over the clothing of the continuous paper production machine with maximum uniformity and regularity. A flow of pulp and water is thus distributed as a thin film of variable width according to the dimensions of the machine, with uniform characteristics in the longitudinal and transverse directions.

Two stages take place in the abovementioned continuous machine, felting and drying.

The second stage which takes place in the machine is dewatering, which is carried out by means of the following process: the diluted pulp is deposited on the continuous cloth conveyor belt and passes to a press unit which is designed to continue the process of dewatering the sheet through mechanical pressing systems. From the press unit it passes to the drier which causes the wet sheet to adhere to heated hollow cylinders. This system may be incorporated in or sometimes replaced by other drying systems such as hot air stoves and infrared ray systems.

During this stage of the process the moisture present in the web decreases to values of between 3 and 5.5%.

From the dryer it may pass to the smoothing machine which is designed to smooth the paper and generally improves the graphic qualities of the paper and it finally passes to the Pope winder in which the paper produced is wound into rolls continuously and rolls are changed without interrupting the production cycle.

In the subsequent stage the paper sheet has at least one detergent, preferably a mixture of detergents, added to it by means of spray or other systems typical of paper coating.

In this case the paper wound onto the Pope roller of the continuous machine is rewound (unwound and rewound) on a winder to prepare rolls of optimum size for subsequent treatment with surfactant. In this case the surfactant spray provides water to the paper substrate, which has to be redried, rewound and subdivided into optimum dimensions for final use.

As an alternative the detergent may be added in line in the continuous machine.

According to this invention the detergent is a surfactant, preferably a mixture of detergents. A solution comprising:
 at least one of anionic surfactants, amphoteric surfactants, non-ionic surfactants, cationic surfactants or a mixture thereof in variable proportions in which the maximum dry percentage is preferably 50%;
 optionally a solution of glycerine in a percentage of less than 5%;
 optionally EDTA, citric acid/sodium citrate in a percentage of less than 5% each;
 optionally sorbitol, sodium lactate, sodium carbonate, in a quantity less than 1% each;
 optionally perfumed essences as 0.1% and essential oils in a concentration below 0.3%;
 is added to the paper according to this invention.

A sheet of paper uniformly impregnated with the substances described above is thus obtained.

The sheets are obtained and again dried by means of hot air jets at a temperature of between 80 and 250° C. depending upon the weight of the paper produced.

In a particular embodiment the continuous sheet of paper obtained may be wound into rolls in the winding section by means of a core which acts as a support around which the paper is wound. Thus a roll of variable weight and the desired width, which is not greater than the useful width of the machine, is produced.

Subsequently the roll of soaped paper may be unrolled and rewound into smaller rolls of various widths and lengths, cut, stacked and packaged according to market requirements.

In a particular embodiment the roll comprises preformed sheets, which may then be used by stacking them one upon the other from the aforesaid roll.

The final stages in the process described above (from unrolling to packaging or any form of packaging) may also be performed through an automated continuous industrial system.

During all the abovementioned stages of the process the soaped paper product does not suffer any deterioration or malformation of any kind. In particular the paper sheet may be wound and unrolled at will without the latter in any way affecting its characteristics. Thanks to the use of the process according to this invention the presence of cleansing agents does not in fact have an adverse effect on the flexibility characteristics of the paper.

The soaped soluble paper obtained using the process described hitherto has a uniform colour, with a smooth surface finish, which can be inked, printed and machined.

This paper disaggregates when used in water. The process of disaggregation of the paper begins as soon as it is soaked and gives rise to complete dissolution, with simultaneous release of the soap.

In one embodiment of the invention the soluble soaped paper obtained is used to clean the hands or other parts of the body, which are suitably soaped when they come into contact therewith.

This paper is also characterised in that it can be written on with pens and/or pencils and may be printed using existing printing technology.

As mentioned, the paper according to this invention may have various uses which make use of the detergent effect and has the advantage that it disaggregates completely in aqueous liquids, without leaving residues, giving an impression of dissolution.

A preferred embodiment provides for use of the said paper to clean the human body, in particular the skin. In this case suitable detergents will be used, in particular those compatible with contact with the skin.

Another embodiment of this invention provides for use of the paper in its edible form to act as a vehicle for active ingredients and/or medicinal ingredients which have to be taken orally. In this case normal known techniques of incorporating these ingredients may be used. In the case of external use disinfectants for external use, anti-inflammatories and softeners may for example be incorporated, and the detergent will be selected in accordance with the active ingredient incorporated.

Another embodiment of this invention provides for the use of this paper to act as a vehicle for products which make it possible to wash garments of different colours in a washing machine. In this case the detergents may be those normally used in the domestic and industrial sector for washing clothing and laundry in water.

Another embodiment of this invention provides for use of the paper with detergents for domestic or industrial use, for example detergents for dishwashers.

Another embodiment of this invention provides for the use of this paper with special detergents, for example hand washing creams. A paper substrate according to this invention will be of a suitable weight.

The paper according to this invention comprising at least one domestic or industrial detergent according to the uses described above falls within the objects of this invention.

The following examples will further illustrate the invention.

EXAMPLES

Example 1

Preparation of Soaped Soluble Paper

The soluble paper substrate is prepared by mixing the following components in a pulper with stirring at ambient temperature for 30 minutes; bleached eucalyptus chemical pulp 13.3% by weight, sodium salt of carboxymethylcellulose 85.4% by weight and debonding agent 1.3% by weight. The concentration of the fibre in water (consistency) is 1% by weight (1 liter of water, 10 g of fibre). At the end of the process a soluble paper of a weight corresponding to 70 g/m$^2$ is obtained. The composition by weight of the paper so obtained is as follows: bleached eucalyptus chemical pulp 86.4% by weight, sodium salt of carboxymethylcellulose 8.3% by weight and debonding agent 5.3% by weight. The roll of paper is subsequently impregnated with an aqueous solution of surfactant having a dry weight of 50% using a spray system. The surfactants used are sodium lauryl ether sulphate and lauramidopropyl betaine in a weight ratio of 1 to 1. The quantity of surfactant applied to the paper is 8 g/m$^2$. The soaped paper is subsequently printed and may be prepared as desired.

Example 2

Preparation of Soaped Soluble Paper

The soluble paper substrate is prepared by mixing the following components in a pulper with stirring at ambient temperature for 30 minutes: bleached eucalyptus chemical pulp 8.9% by weight, bleached conifer chemical pulp 4.4% by weight, sodium salt of carboxymethylcellulose 85.4% by weight and debonding agent 1.3% by weight. The concentration of the fibre in water (consistency) is 1% by weight (1 liter of water, 10 g of fibre). At the end of the process a soluble paper having a weight corresponding to 70 g/m$^2$ is obtained. The composition by weight of the paper so obtained is as follows: bleached eucalyptus chemical pulp 57.6% by weight, bleached conifer chemical pulp 28.8% by weight, sodium salt of carboxymethylcellulose 8.3% by weight and debonding agent 5.3% by weight. The paper is subsequently impregnated with an aqueous solution of surfactant having a dry weight of 50% using a spray system. The surfactants used are sodium lauryl ether sulphate and lauramidopropyl betaine in a weight ratio of 1 to 1. The quantity of surfactant applied to the paper is 8 g/m$^2$. The soaped paper is subsequently printed and may be prepared as desired.

Example 3

Production of Soluble Soaped Paper

A roll produced with the specifications in Example 1 is subsequently impregnated with an aqueous solution of surfactant, having a dry weight of 50%, using a spray system. The surfactants used are sodium lauryl ether sulphate, lauramidopropyl betaine and benzalkonium chloride, in the following percentages by weight respectively 49.6, 49.6, and 0.8%. The quantity of surfactant applied to the paper is 8 g/m$^2$. The soaped paper is subsequently printed and cut into rolls of the desired size.

Example 4

Use of a Soluble Soaped Paper

FIG. 2 shows a practical application of the paper to which this invention relates.

A sheet of soluble soaped cleansing paper is separated from the roll (FIG. 2a) and is subsequently used under running water (FIG. 2b).

The invention disaggregates completely, dissociating into single fibres, suitably soaping the hands and the parts of the body of the individual using it (FIG. 2c).

Finally FIG. 2d shows total disaggregation of the paper according to this invention, with consequent normal rinsing. The user perceives the disaggregation as dissolution.

The invention claimed is:

1. A soaped paper, comprising
(a) a disaggregatable paper comprising 50-90% by weight of cellulose fibers and 3-20% by weight of a disaggregating agent selected from the group consisting of polymers based on polyvinyl pyrrolidone, polyethylene glycol, xanthan gum, guar gum, polyquaternium polymers, pullulan, hydroxypropylmethyl cellulose, hydroxyethyl cellulose, hydroxypropyl cellulose, gelatine, sodium salt of carboxymethylcellulose, polyvinyl alcohol, sodium alginate, gum tragacanth, acacia gum, gum arabic, polyacrylic acid, methylmethacrylate copolymer, carboxyvinyl polymer, amylases, natural and modified starches, aluminium starch octenylsuccinate, hydroxypropyl starch phosphates, high amylase starch, high amylase hydroxypropylate starch, dextrin, pectin, chitin, chitosan, levan, elsinan, collagen, zein, gluten, soya protein isolate, milk protein isolate, casein, carob bean gum, karaya gum, carrageenan, gellan gum, agar, alginic acid and alginates, furcellaran, polyhydroxy acid polymers, polysaccharides, and mixtures thereof; and
(b) at least one detergent added to the disaggregatable paper.

2. The soaped paper according to claim 1, wherein the disaggregatable paper comprises between 80 and 90% by weight of cellulose fibers.

3. The soaped paper according to claim 1, wherein the disaggregatable paper comprises between 5 and 13% by weight of the disaggregating agent.

4. The soaped paper according to claim 1, wherein the disaggregatable paper further comprises at least one of the following components:
d. 2-8% by weight of a debonding agent;
e. 0.01-0.05% by weight of a dye;
f. 0.1-20% by weight of a mineral pigment; and
g. 0.1-5% by weight of a retention agent.

5. The soaped paper according to claim 4, wherein the disaggregatable paper comprises
57.6% by weight of cellulose fibers from bleached eucalyptus chemical pulp,
28.8% by weight of cellulose fibers from bleached conifer chemical pulp, and
8.3% by weight of a sodium salt of carboxymethylcellulose, and further comprises
5.3% by weight of a debonding agent, and the disaggregatable paper has a weight of 70 g/m$^2$; and
wherein the detergent comprises sodium lauryl ether sulphate and lauramidopropyl betaine in a weight ratio of 1 to 1, and is added to the disaggregatable paper at a quantity of 8 g/m$^2$.

6. The soaped paper according to claim 4, wherein the paper comprises
86.4% by weight of cellulose fibers from bleached eucalyptus chemical pulp, and
8.3% by weight of a sodium salt of carboxymethylcellulose, and further comprises
5.3% by weight of a debonding agent, and the disaggregatable paper has a weight of 70 g/m$^2$; and
wherein the detergent comprises 49.6% by weight of sodium lauryl ether sulphate, 49.6% by weight of lauramidopropyl betaine, and 0.8% by weight of benzalkonium chloride, and is added to the disaggregatable paper at a quantity of 8 g/m$^2$.

7. The soaped paper according to claim 1, in which the disaggregating agent comprises the sodium salt of carboxymethylcellulose.

8. The soaped paper according to claim 1, wherein the disaggregatable paper has a weight between 20 and 500 g/m$^2$.

9. The soaped paper according to claim 1, wherein the disaggregatable paper comprises
86.4% by weight of cellulose fibers from bleached eucalyptus chemical pulp, and
8.3% by weight of a sodium salt of carboxymethylcellulose, and further comprises
5.3% by weight of a debonding agent, and the disaggregatable paper has a weight of 70 g/m$^2$; and
wherein the detergent comprises sodium lauryl ether sulphate and lauramidopropyl betaine in a weight ratio of 1 to 1, and is added to the disaggregatable paper at a quantity of 8 g/m$^2$.

10. The soaped paper according to claim 1, wherein the at least one detergent is selected from the group consisting of detergents for dishwashers, detergents for the washing of clothes, and hand washing creams.

11. The soaped paper according to claim 1, further comprising a disinfectant.

12. A roll of the soaped paper of claim 1.

13. The roll according to claim 12, wherein the soaped paper comprises preformed sheets.

14. A pack, comprising sheets of the soaped paper according to claim 1 and a package.

15. A process for producing a roll of the soaped paper according to claim 1, comprising mixing the cellulose fibers together with the disaggregating agent to form a mixture; dewatering the mixture to form a disaggregatable paper, adding at least one detergent to the disaggregatable paper, thereby forming the soaped paper, and rolling the soaped paper.

16. The method according to claim 15, wherein the method further comprises treating the surface of the disaggregatable paper with a size press or a film press, and smoothing the disaggregatable paper.

17. A method for washing the skin, comprising contacting the skin with the soaped paper of claim 1.

18. A method for disinfecting the skin, comprising contacting the skin with the soaped paper of claim 11.

19. A method for washing garments, comprising contacting the garments with the soaped paper of claim 1.

20. A method for washing dishes, comprising contacting the dishes with the soaped paper of claim 1.

* * * * *

UNITED STATES PATENT AND TRADEMARK OFFICE
CERTIFICATE OF CORRECTION

PATENT NO. : 9,506,022 B2
APPLICATION NO. : 14/377812
DATED : November 29, 2016
INVENTOR(S) : Danilo Ronco et al.

Page 1 of 1

It is certified that error appears in the above-identified patent and that said Letters Patent is hereby corrected as shown below:

The (30) Foreign Application Priority Data should read:

February 24, 2012  (IT) ........................................CN2012A000004

Signed and Sealed this
Seventh Day of February, 2017

Michelle K. Lee
*Director of the United States Patent and Trademark Office*